US010952639B2

(12) United States Patent
Inoue (10) Patent No.: US 10,952,639 B2
(45) Date of Patent: Mar. 23, 2021

(54) MASK

(71) Applicant: NIHON KOHDEN CORPORATION, Tokyo (JP)

(72) Inventor: Masayuki Inoue, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 15/469,944

(22) Filed: Mar. 27, 2017

(65) Prior Publication Data

US 2017/0196512 A1 Jul. 13, 2017

Related U.S. Application Data

(63) Continuation of application No. 14/506,351, filed on Oct. 3, 2014, now Pat. No. 9,775,541.

(30) Foreign Application Priority Data

Oct. 9, 2013 (JP) .............................. JP2013-212348

(51) Int. Cl.
*A61B 5/097* (2006.01)
*A61B 5/08* (2006.01)
(Continued)

(52) U.S. Cl.
CPC .............. *A61B 5/097* (2013.01); *A61B 5/082* (2013.01); *A61B 5/0833* (2013.01);
(Continued)

(58) Field of Classification Search
CPC ............ A61M 16/009; A61M 16/0003; A61M 16/06–0694; A61M 2016/103
See application file for complete search history.

(56) References Cited

U.S. PATENT DOCUMENTS 4,454,880 A 6/1984 Muto et al.
5,645,047 A * 7/1997 Akers .................. A62B 18/025
128/201.28

(Continued)

FOREIGN PATENT DOCUMENTS

CN 101437565 A 5/2009
CN 102049081 A 5/2011
(Continued)

OTHER PUBLICATIONS

Japanese Office Action issued in Patent Application No. JP-2013-212348 dated Nov. 29, 2017.
(Continued)

*Primary Examiner* — Valerie L Woodward
(74) *Attorney, Agent, or Firm* — Pearne & Gordon LLP (57) ABSTRACT

A mask configured to be attached to the face of a subject includes a wall section that defines an internal space and covers at least a portion of a nose and a mouth of the subject, an expired gas introduction section that is disposed in the internal space and introduce the subject's expired gas, and a communication section defining a communication channel through which the subject's expired gas introduced from the expired gas introduction section is introduced into an expired gas concentration detection sensor. The position of the expired gas introduction section in the internal space is variable.

19 Claims, 6 Drawing Sheets

(51) Int. Cl.
*A61M 16/00* (2006.01)
*A61M 16/08* (2006.01)
*A61M 16/06* (2006.01)
*A61B 5/00* (2006.01)
*A61B 5/083* (2006.01)
*A61B 5/087* (2006.01)
*A61M 16/10* (2006.01)

(52) U.S. Cl.
CPC .......... *A61B 5/0873* (2013.01); *A61B 5/682* (2013.01); *A61B 5/6803* (2013.01); *A61B 5/6819* (2013.01); *A61M 16/0003* (2014.02); *A61M 16/06* (2013.01); *A61M 16/085* (2014.02); *A61B 5/083* (2013.01); *A61M 2016/103* (2013.01)

(56) References Cited

U.S. PATENT DOCUMENTS

| | | | |
|---|---|---|---|
| 5,857,460 A * | 1/1999 | Popitz | A61M 16/06 128/204.22 |
| 7,004,163 B2 * | 2/2006 | Nashed | A61M 16/00 128/201.22 |
| 7,004,168 B2 * | 2/2006 | Mace | A61M 16/06 128/203.12 |
| 7,568,483 B2 | 8/2009 | Scarberry et al. | |
| 8,042,540 B2 * | 10/2011 | McDonald | A61M 16/06 128/205.25 |
| 8,534,278 B2 * | 9/2013 | Colman | A61M 16/0488 128/200.26 |
| 9,393,376 B2 * | 7/2016 | Inoue | A61B 5/682 |
| 9,775,541 B2 * | 10/2017 | Inoue | A61B 5/097 |
| 2002/0122746 A1 * | 9/2002 | Yamamori | G01N 1/22 422/83 |
| 2006/0081243 A1 | 4/2006 | McDonald | |
| 2006/0081248 A1 | 4/2006 | McDonald | |
| 2006/0196510 A1 | 9/2006 | McDonald et al. | |
| 2006/0247551 A1 * | 11/2006 | Yamamori | A61B 5/0836 600/532 |
| 2006/0249160 A1 * | 11/2006 | Scarberry | A61B 5/0836 128/207.13 |
| 2008/0196715 A1 * | 8/2008 | Yamamori | A61B 5/0836 128/203.12 |
| 2008/0319334 A1 | 12/2008 | Yamamori | |
| 2009/0069646 A1 | 3/2009 | Yamamori et al. | |
| 2011/0015534 A1 * | 1/2011 | Yamamori | A61B 5/0836 600/532 |
| 2011/0094513 A1 * | 4/2011 | Takatori | A61M 16/06 128/205.25 |
| 2011/0315141 A1 | 12/2011 | Lavi et al. | |
| 2012/0067349 A1 * | 3/2012 | Barlow | A61M 16/0633 128/205.25 |
| 2017/0028154 A1 | 2/2017 | Takatori et al. | |
| 2017/0112414 A1 | 4/2017 | Yamamori | |

FOREIGN PATENT DOCUMENTS

| | | |
|---|---|---|
| CN | 102421486 A | 4/2012 |
| JP | S62-92802 U | 6/1987 |
| JP | 2009-172347 A | 8/2009 |
| JP | 2011-036643 A | 2/2011 |
| JP | 2011-115543 A | 6/2011 |
| WO | 2013-066195 A1 | 5/2013 |

OTHER PUBLICATIONS

Extended European Search Report Issued in Patent Application No. EP 14 18 7771 dated Feb. 2, 2015.
Chinese Office Action issued in Patent Application No. CN 201410524537.8 dated Oct. 30, 2017.
Japanese Office Action issued in Patent Application No. JP 2013-212348 dated Apr. 25, 2017.
Japanese Office Action issued in Patent Application No. JP-2013-212348 dated May 8, 2018.
Communication pursuant to Article (4(3) EPC issued in Patent Application No. EP 14 187 771 dated Jun. 11, 2019.

* cited by examiner

MASK

CROSS REFERENCE TO RELATED APPLICATION

This application is based on Japanese Patent Applications No. 2013-212348 filed on Oct. 9, 2013, the contents of which are incorporated herein by reference.

BACKGROUND

The presently disclosed subject matter relates to a mask which is attached to the face of a subject so as to introduce the expired gas of the subject to an expired gas concentration detection sensor.

As an example of such a mask, Patent Document 1 discloses an oxygen mask which includes a wall section, an expired gas introduction section, and a communication section. The wall section defines an internal space of the mask so as to cover at least a portion of a nose and a mouth of the subject. The expired gas introduction section is disposed in the internal space so as to introduce the expired gas of the subject. The communication section defines a communication channel which is supported by the wall section and through which the expired gas of the subject is introduced into an expired gas concentration detection sensor.

[Patent Document 1] JP-A-2011-115543

The shape of the faces to which such a mask is attached is different for each subject. Particularly, the shape of a nose to which the expired gas introduction section is in close proximity is different for each subject. Owing to this difference in facial shapes, the expired gas of the subject is often not surely introduced into the expired gas concentration detection sensor.

Accordingly, the presently disclosed subject matter aims as providing the technique to make sure the introduction of the expired gas of a subject to an expired gas concentration detection sensor regardless of the subjects' facial shapes.

SUMMARY (1) According to an aspect of the presently disclosed subject matter, a mask configured to be attached to the face of a subject includes a wall section that defines an internal space and covers at least a portion of a nose and a mouth of the subject, an expired gas introduction section that is disposed in the internal space and introduce the subject's expired gas, and a communication section that defines a communication channel through which the subject's expired gas introduced from the expired gas introduction section is introduced into an expired gas concentration detection sensor. The position of the expired gas introduction section in the internal space is variable.

According to this configuration, the expired gas introduction section is movable to the position where the expired gas of the subject can be surely introduced. Thus, the expired gas can be surely introduced into the expired gas concentration detection sensor regardless of subject's facial shapes.

(10) According to another aspect of the presently disclosed subject matter, a mask configured to be attached to the face of a subject includes a wall section that defines an internal space and covers at least a portion of a nose and a mouth of the subject, an expired gas introduction section that is disposed in the internal space and introduces the subject's expired gas, and a communication section that defines a communication channel through which the subject's expired gas introduced from the expired gas introduction section is introduced into an expired gas concentration detection sensor. The expired gas introduction section includes a partition part which defines a first opening part opening against the subject's face when the subject wears the mask, and a second opening part opening upwards.

According to this configuration, the expired gas from the mouth can be surely introduced into the communication channel through the first opening part, and the expired gas from the nose can be surely introduced into the communication channel through the second opening part. Particularly, the second opening part opens upwards, so that the expired gas from the nose can be surely introduced into the communication channel therethrough, regardless of the difference in the nasal shapes of subjects. Accordingly, the expired gas can be surely introduced into the expired gas concentration detection sensor regardless of subject's facial shapes.

(2) The mask of the configuration (1) further includes a bridge part that connects the wall section and the expired gas introduction section, and the bridge part is stretchable.

A portion of the face (particularly, the nose) may often contact the expired gas introduction section depending upon the subjects' facial shapes. In this case, with the bridge part being extended, the expired gas introduction section moves forward in the internal space of the wall section, thereby possibly preventing the generation of an excessive contact pressure against the subject's face. This avoids making the subject uncomfortable, ensuring that the mask is readily maintained at a proper attachment position. Accordingly, the expired gas can be surely introduced into the expired gas concentration detection sensor regardless of subjects' facial shapes.

(3) In the mask of the configuration (2), the bridge part includes a corrugated part.

According to this configuration, it is possible to obtain a great degree of extension while securing the strength to support the expired gas introduction section. This more securely avoids making the subject uncomfortable, and ensures that a proper disposition of the expired gas introduction section is maintained. Accordingly, the expired gas can be surely introduced into the expired gas concentration detection sensor regardless of subjects' facial shapes.

(4) In the mask of any one of the configurations (1) to (3), the communication section and the expired gas introduction section are coupled in such a manner as to be relatively movable with respect to each other.

According to this configuration, the initial position of the expired gas introduction section in the internal space can be changed depending upon the facial shape of subject to which the mask is attached. For example, the expired gas can be introduced into the position at which the expired gas introduction section cannot contact the subject's nose or into which the expired gas can be more surely introduced. Accordingly, the expired gas can be surely introduced into the expired gas concentration detection sensor regardless of subjects' facial shapes.

(5) In the mask of any one of the configurations (1) to (4), the expired gas introduction section is supported by the communication section, and the mask further includes an adjusting mechanism that adjusts a supporting position at which the communication section is supported by the wall section.

According to this configuration, the initial position of the expired gas introduction section in the internal space can be changed depending upon the facial shape of subject to which the mask is attached. For example, the expired gas can be introduced into the position at which the expired gas introduction section cannot contact the subject's nose or into which the expired gas can be more surely introduced. Accordingly, the expired gas can be surely introduced into the expired gas concentration detection sensor regardless of subjects' facial shapes.

(6) In the mask of the configuration (5), the adjusting mechanism includes a mechanism that adjusts the supporting position by elastic deformation of the wall section.

According to this configuration, there is no need to provide a complicated structure for enabling the position of the communication section supported by the wall section to be able to be regulated. Accordingly, the expired gas can be surely introduced into the expired gas concentration detection sensor regardless of the difference in the subjects' facial shapes, without excessively increasing the cost.

(8) The mask of any one of the configurations (1) to (7) further includes a sensor support that supports an expired gas concentration detection sensor which includes a light-emitting device and a light-receiving device so that light emitted from the light-emitting device passes across a light-passing portion of the communication channel. The sensor support has a vent hole by which the outside of the wall section communicate with the communication channel, and the vent hole is formed on the sensor support so as not to overlap with the light-passing portion of the communication channel in a passing direction of the light-passing portion.

According to this configuration, it is possible to prevent the introduction of external air with ventilation. This prevents the inverse affection of the introduction of external air on the detection of the expired gas concentration in the detection space. Further, it is possible to discharge the expired gas quickly by means of a vent hole. Accordingly, along with the above-mentioned function of regulating the position of the expired gas introduction section, there is provided a function of precisely detecting the concentration of the subject's expired gas.

(9) The mask of the configuration (8) further includes an oxygen-supply section that communicates with the internal space and holds one end of an oxygen-supply tube, and a holding section that detachably holds a signal line connected to the expired gas concentration detection sensor. The oxygen-supply section and the holding section are arranged symmetrically with respect to the sensor support which is interposed between the oxygen-supply section and the holding section.

According to this configuration, the oxygen-supply tube and the signal line can be drawn symmetrically in the left and right sides of the mask, so it is possible to stabilize the posture of the mask with respect to the subject's face. Accordingly, along with the above-mentioned function of regulating the position of the expired gas introduction section, there is provided both the function of precisely detecting the concentration of the subject's expired gas and the function of stably supplying oxygen to the subject.

When combined with the configuration having the bridge part which connects the wall section and the inspired air introduction section, the bridge part scatters oxygen to be introduced into the internal space so as to homogenize the concentration of oxygen in the internal space. Further, oxygen to be injected in the internal space from the oxygen-supply section does not directly contact the subject's face, thereby preventing the skin from becoming dry.

DETAILED DESCRIPTION OF EMBODIMENTS

Exemplary embodiments of the presently disclosed subject matter will now be described in detail with reference to the accompanying drawings. The terms 'right side' and 'left side' used herein respectively denote the right direction and left direction seen from a subject who wears the mask.

Figure 1:
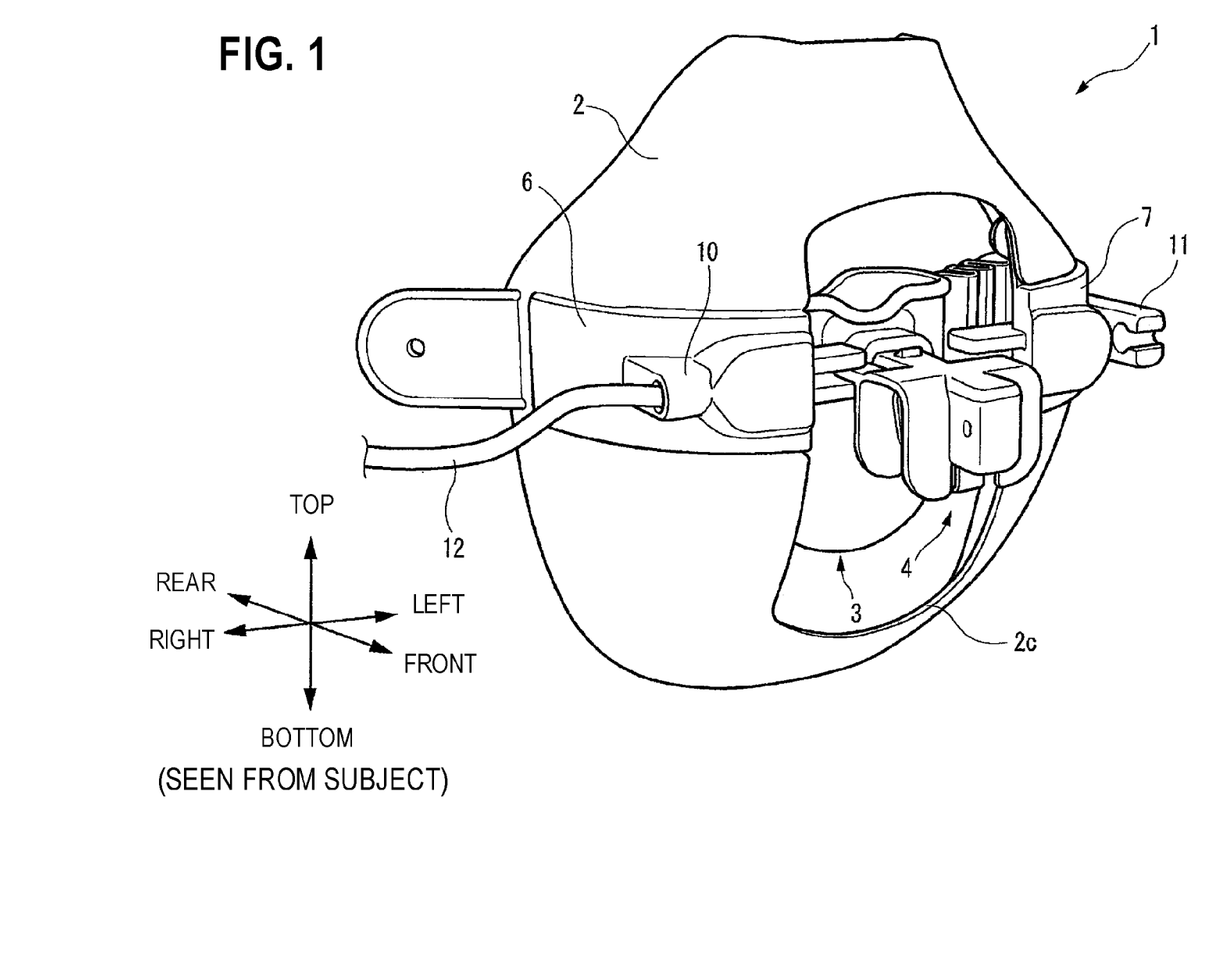
FIG. 1 is a front perspective view of a mask according to an embodiment of the presently disclosed subject matter.
Figure 2:
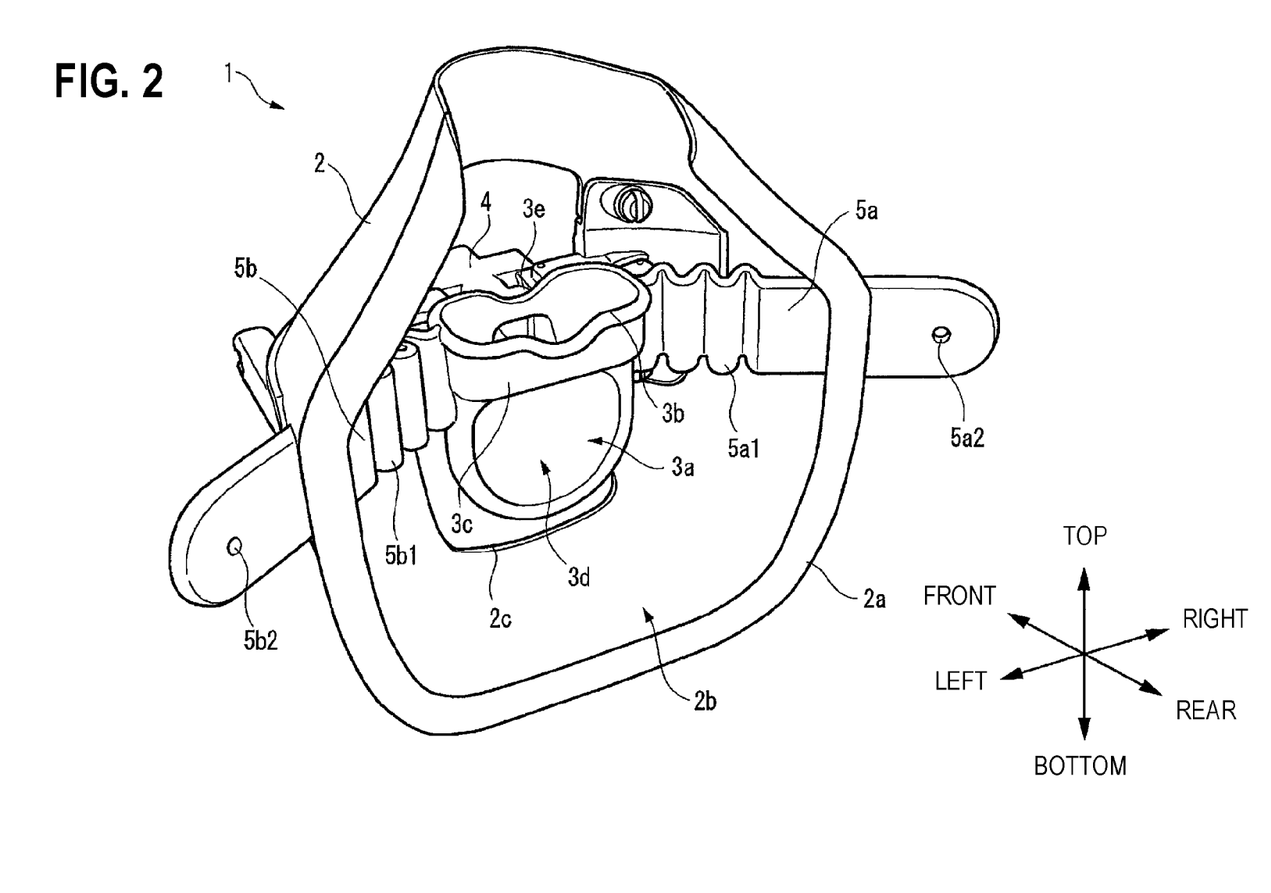
FIG. 2 is a rear perspective view of the mask of FIG. 1.

FIG. 1 is a perspective view showing an appearance of a mask 1 according to an embodiment of the presently disclosed subject matter when viewed obliquely from the right front side thereof. FIG. 2 is a perspective view showing an appearance of the mask 1 when viewed obliquely from the left rear side thereof. The mask 1 to be attached to the subject's face includes a wall section 2, an expired gas introduction section 3, and a communication section 4.

The wall section 2 is formed into a dome-shaped appearance which is composed of an elastic material. The wall section 2 has the size and shape which cover at least a portion of a nose and a mouth of the subject. An edge part 2a on the rear side of the wall section 2 contacts the subject's face. The wall section 2 defines an internal space 2b therein. The wall section 2 has an opening 2c on the front side thereof. The opening 2c allows the internal space 2b and the outside of the wall section to communicate with each other.

The expired gas introduction section 3 is disposed in the internal space 2b of the wall section 2. The expired gas introduction section 3 is provided with a partition part 3c which defines first and second opening parts 3a and 3b. The first opening part 3a opens towards the face of the subject who wears the mask 1. The second opening part 3b opens upwards when the mask is attached to the face of the subject. When the mask 1 is attached, a mouth and a nose of the subject are respectively provided in close proximity to the first and second opening parts 3a and 3b.

The expired gas introduction section 3 defines an introduction space 3d which communicates with the first and second opening parts 3a and 3b. The expired gas introduction section 3 introduces the expired gas from the mouth and nose of the subject into the introduction space 3d through the first and second opening parts 3a and 3b. The expired gas introduction section 3 is provided on the front side with a connection part 3e which defines a communication channel communicating with the introduction space 3d.

The communication section 4 is supported by the wall section 2. The rear side of the communication section 4 is coupled with the connection part 3e of the expired gas introduction section 3. The communication section 4 defines a communication channel therein. The communication channel communicates with the introduction space 3d of the expired gas introduction section 3 via the connection part 3e. The communication channel introduces the expired gas from the expired gas introduction section 3 into the expired gas concentration detection sensor.

In the mask 1 according to the present embodiment, the expired gas introduction section 3 is disposed in the internal space 2b of the wall section 2 so as to be repositionable within the internal space 2b.

According to this configuration, the expired gas introduction section 3 is movable to a place to which the subject's expired gas is surely introduced. Accordingly, the expired gas can be surely introduced into the expired gas concentration detection sensor regardless of subject's facial shapes.

The expired gas introduction section 3 has the first and second opening parts 3a and 3b divided by the partition part 3c. The first opening part 3a opens towards the face of the subject who wears the mask 1. The second opening part 3b opens upwards when the mask is attached to the face of the subject. According to this configuration, the expired gas from the mouth and the nose can be surely introduced into the introduction space 3d through the first and second opening parts 3a and 3b, respectively. Particularly, since the second opening part 3b opens upwards, the expired gas from the nose is surely introduced into the introduction space 3d regardless of the difference in subject's nasal shapes. Accordingly, the expired gas is surely introduced into the expired gas concentration detection sensor regardless of subject's facial shapes.

A detailed configuration for variable displacement of the expired gas introduction section 3 in the internal space 2b of the wall section 2 will now be described.

As shown in FIG. 2, the mask 1 includes a right bridge part 5a and a left bridge part 5b. The right bridge part 5a connects the right side of the wall section 2 and the right side of the expired gas introduction section 3. The left bridge part 5b connects the left side of the wall section 2 and the left side of the expired gas introduction section 3. The right and left bridge parts 5a and 5b are respectively stretchable in their longitudinal directions. Specifically, the right and left bridge parts 5a and 5b is each provided with a corrugated part 5a1, 5b1. The corrugated parts 5a1 and 5b1 respectively allow the right and left bridge parts 5a and 5b to be flexibly extended in the respective longitudinal directions.

A right end of the right bridge part 5a has an extension which further extends out of the right side of the wall section 2, and the extension is provided with a through-hole 5a2. A left end of the left bridge part 5b has an extension which further extends out of the left side of the wall section 2, and the extension is provided with a through-hole 5b2. The through-holes 5a2 and 5b2 are elements through which strings pass so that the strings are hung around subject's ears to hold the mask 1 over the subject's face.

A portion of the face (particularly, the nose) may often contact the expired gas introduction section 3 depending upon the subject's facial shapes. In this case, with the right and left bridge parts 5a and 5b being extended, the expired gas introduction section 3 moves forward in the internal space 2b of the wall section 2, thereby possibly preventing the generation of an excessive contact pressure against the subject's face. This avoids making the subject uncomfortable, ensuring that the mask 1 is readily maintained at a proper attachment position. Accordingly, the expired gas is surely introduced into the expired gas concentration detection sensor regardless of subject's facial shapes.

Particularly, the right and left bridge parts 5a and 5b are respectively provided with corrugated parts 5a1 and 5b1, enabling the right and left bridge parts 5a and 5b to be stretchable, so that it is possible to obtain a great degree of extension while securing the strength to support the expired gas introduction section 3. This more securely avoids making the subject uncomfortable, and ensures that a proper disposition of the expired gas introduction section 3 is maintained. Accordingly, the expired gas can be surely introduced into the expired gas concentration detection sensor regardless of subject's facial shapes.

As shown in FIG. 1, the wall section 2 has right and left support parts 6 and 7 on the front side thereof. The communication section 4 is interposed between the right and left support parts 6 and 7 and is supported by the wall section 2.

Figure 3A:
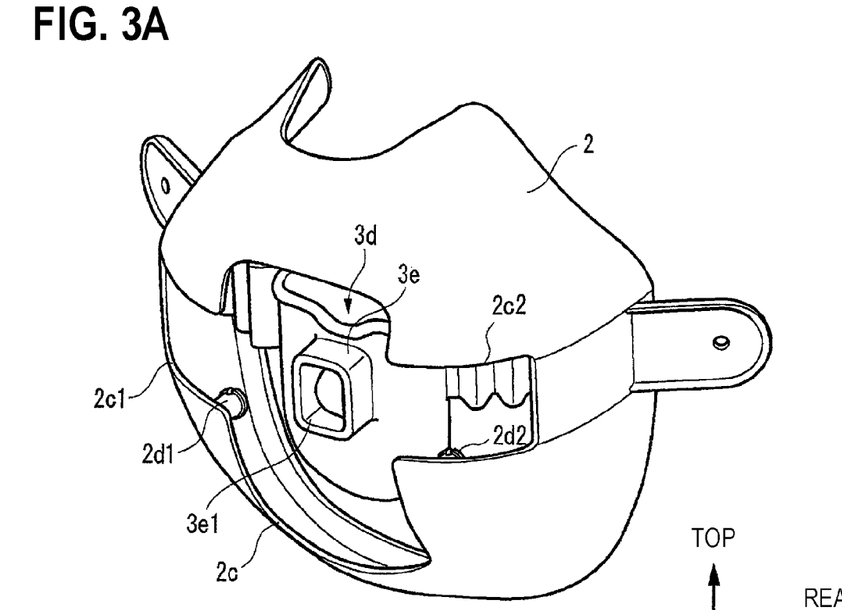
FIGS. 3A and 3B are front perspective views of portions of the mask of FIG. 1.
Figure 3B:
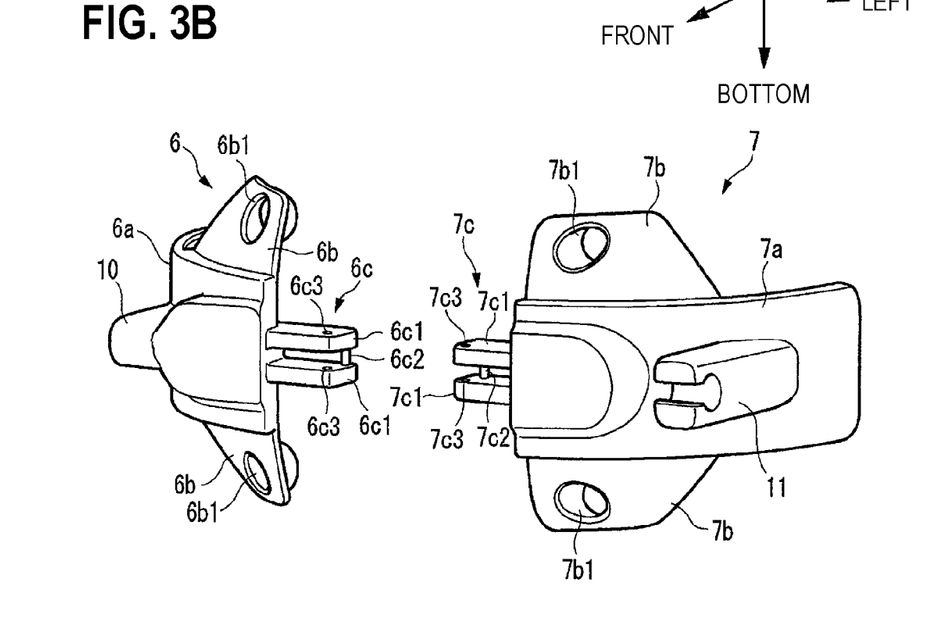

FIG. 3A is a perspective view showing an appearance of the mask 1 with the communication section 4 and the right and left support parts 6 and 7 removed. FIG. 3B is a perspective view showing an appearance of the right and left support parts 6 and 7.

A shown in FIG. 3A, an opening 2c formed on the front side of the wall section 2 has a right slit 2c1 extending in the right side and a left slit 2c2 extending in the left side. A base end portion of the right slit 2c1 is provided on upper and lower sides thereof with right hook protrusions 2d1 (the lower side protrusion is only shown in FIG. 3A, and the upper side protrusion is shown in FIG. 2) which extend rearwards. A base end portion of the left slit 2c2 is provided on upper and lower sides thereof with left hook protrusions 2d2 (the lower side protrusion is only shown in FIG. 3A) which extend rearwards.

The expired gas introduction section 3 is provided on the front side with a connection part 3e which extends forwards. A circumferential wall constituting the connection part 3e defines a communication channel which communicates with the introduction space 3d. The connection part 3e is provided on the front end surface with an engaging part 3e1 which protrudes inwards from the inner surface of the circumferential wall, narrowing the communication channel.

As shown in FIG. 3B, the right support part 6 includes a right base 6a, a pair of right engaging pieces 6b, and a right connector 6c. The right base 6a extends rearwards in an arc form (see FIG. 1). The right support part 6 is made of a harder material than the wall section 2, but a rear end portion of the right base 6a has flexibility with which the rear end portion coincides with the shape of the wall section to which the right support part is attached. The pair of right engaging pieces 6b extends upwards and downwards from the front end surface of the right base 6a. The respective right engaging piece 6b is provided with a right through-hole 6b1. The right connector 6c is provided with a pair of right plate portions 6c1 which extends leftwards from the front end surface of the right base 6a. The pair of right plate portions 6c1 is connected by a right rod portion 6c2 which extends vertically. The respective right plate portion 6c1 is provided with a right through-hole 6c3.

The left support part 7 includes a left base 7a, a pair of left engaging pieces 7b, and a left connector 7c. The left base 7a extends rearwards in an arc form. The left support part 7 is made of a harder material than the wall section 2, but a rear end portion of the left base 7a has flexibility with which the rear end portion coincides with the shape of the wall section to which the left support part is attached. The pair of left engaging pieces 7b extends upwards and downwards from the front end surface of the left base 7a. The respective left engaging piece 7b is provided with a left through-hole 7b1. The left connector 7c is provided with a pair of left plate portions 7c1 which extends leftwards from the front end surface of the left base 7a. The pair of left plate portions 7c1 is connected by a left rod portion 7c2 which extends vertically. The respective left plate portion 7c1 is provided with a left through-hole 7c3.

The right support part 6 is mounted in such a manner that the pair of right engaging pieces 6b is disposed on the rear side of the right slit 2c1 of the wall section 2. Here, the respective right engaging protrusions 2d1 are inserted through the right corresponding through-holes 6b1 so as to hold the right support part 6 on the wall section 2. The left support part 7 is mounted in such a manner that the pair of left engaging pieces 7b is disposed on the rear side of the left slit 2c2 of the wall section 2. Here, the respective left engaging protrusions 2d2 are inserted through the left corresponding through-holes 7b1 so as to hold the left support part 7 on the wall section 2.

Figure 4A:
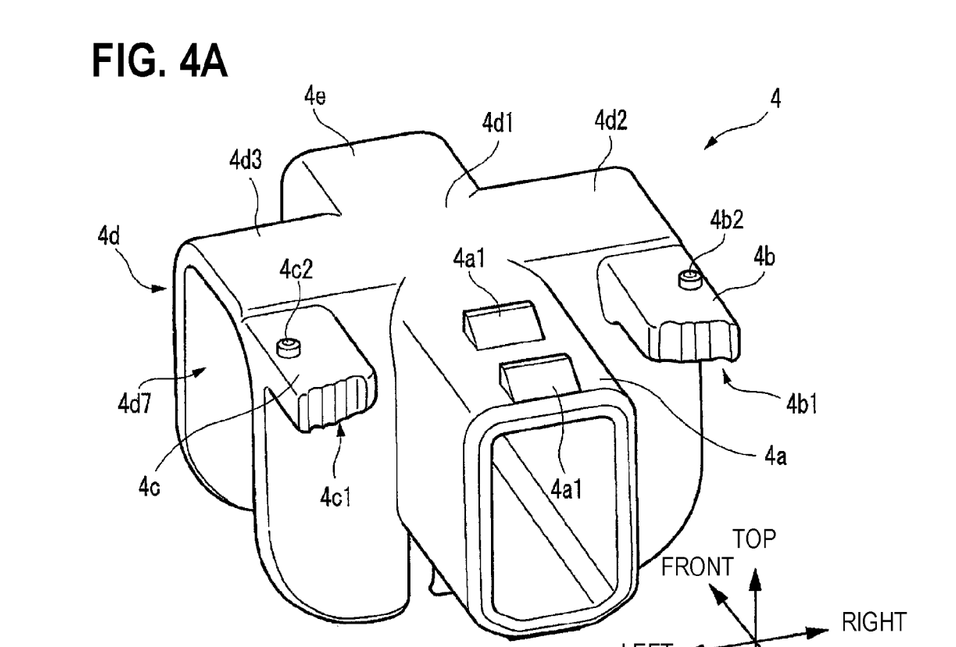
FIGS. 4A and 4B are rear perspective views of a portion of the mask of FIG. 1.

FIG. 4A is a perspective view showing an appearance of the communication section 4 when obliquely viewed from the left rear side thereof. The communication section 4 has a connection part 4a which extends forwards and rearwards from the mask 1. The connection part 4a defines a communication channel therein. The connection part 4a is provided on the outer surface thereof with a plurality of protrusions 4a1, which are arranged in the front-to-rear direction of the mask 1.

A shown in FIGS. 1 and 2, the connection part 4a of the communication section 4 and the connection part 3e of the expired gas introduction section 3 are coupled together, and the communication channel defined by the connection part 4a and the communication channel defined by the connection part 3e communicate with each other. Specifically, the connection parts 4a and 3e are coupled such that the outer surface of the connection part 4a faces against the inner surface of the connection part 3e. Here, the protrusion 4a1 formed on the outer surface of the connection part 4a is engaged with the engaging part 3e1 formed on the front end surface of the connection part 3e, so that the connection part 3e is positioned with respect to the connection part 4a.

The connection part 3e of the expired gas introduction part 3 is composed of a flexible material, and is coupled with the connection part 4a of the communication section 4 in such a manner that the connection part 3e is slidable in the forward-rearward direction of the mask 1. As described above, since the connection part 4a is provided on the outer surface thereof with the plurality of protrusions 4a1 in the forward-rearward direction of the mask 1, the position of the connection part 3e with respect to the connection part 4a is changeable by selecting the protrusion 4a1 to be engaged with the engaging part 3e1 of the connection part 3e. That is, the arrangement of the expired gas introduction section 3 with respect to the communication section 4 is changeable in the forward-rearward direction in the internal space 2b of the wall section 2.

According to this configuration, the initial position of the expired gas introduction section in the internal space is changeable depending upon the facial shape of subject to which the mask is attached. For example, the expired gas introduction section is movable into a position at which the expired gas introduction section does not contact with the subject's nose or into a position at which the expired gas is more surely introduced. Accordingly, the expired gas is surely introduced into the expired gas concentration detection sensor regardless of subject's facial shapes.

As shown in FIG. 4A, the communication section 4 also has right and left connection parts 4b and 4c.

The right connection part 4b is provided on the rear side thereof with a plurality of right grooves 4b1 which extends vertically. The right grooves 4b1 are arranged in the left-right direction of the mask 1. The right connection part 4b is provided on upper and lower sides thereof with right protrusions 4b2 in a pair (the upper-side right protrusion 4b2 is only shown).

The left connection part 4c is provided on the rear side thereof with a plurality of left grooves 4c1 which extends vertically. The left grooves 4c1 are arranged in the left-right direction of the mask 1. The left connection part 4c is provided on upper and lower sides thereof with left protrusions 4c2 in a pair (the upper-side left protrusion 4c2 is only shown).

Figure 4B:
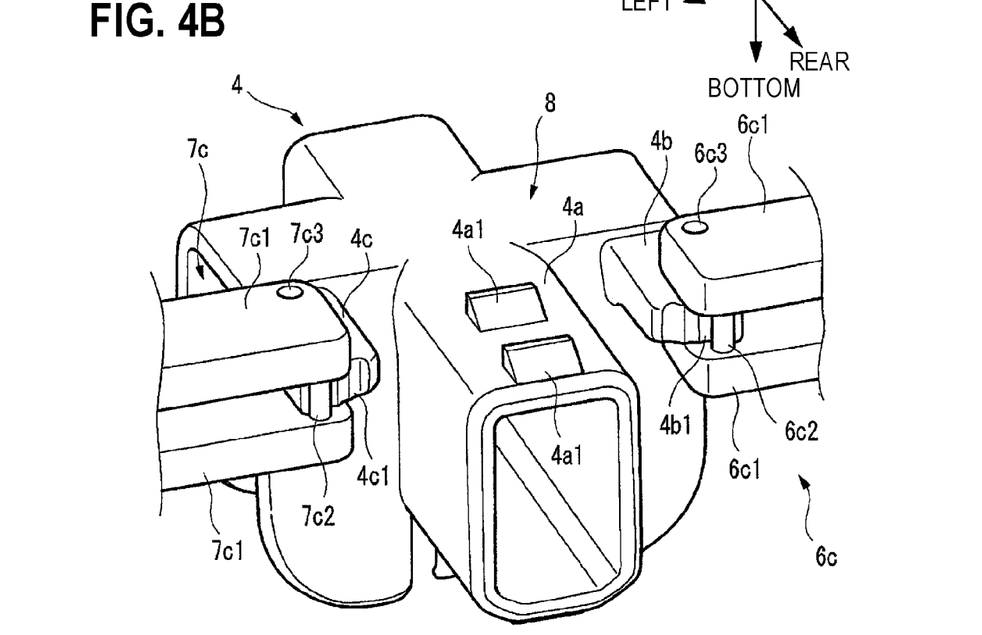

As shown in FIG. 4B, the right connection part 4b is held between the pair of right plate portions 6c1 of the right connector 6c by fitting the pair of right protrusions 4b2 of the right connection part 4b of the communication section 4 into the pair of right through-holes 6c3 of the right connector 6c of the right support part 6. Here, the right rod 6c2 of the right connector 6c is engaged with one of the right grooves 4b1.

Similarly, the left connection part 4c is held between the pair of left plate portions 7c1 of the left connector 7c by fitting the pair of left protrusions 4c2 of the left connection part 4c of the communication section 4 into the pair of left through-holes 7c3 of the left connector 7c of the left support part 7. Here, the left rod 7c2 of the left connector 7c is engaged with one of the left grooves 4c1.

Accordingly, the communication section 4 is interposed between the right and left support parts 6 and 7 and is supported by the wall section 2. Here, the right connection part 4b is able to rotate about the pair of right protrusions 4b2. Similarly, the left connection part 4c is able to rotate about the pair of left protrusions 4c2.

When the right and left support parts 6 and 7 are pressed from the left and right sides, the wall section 2 is deformed such that the width in the left-right direction is narrowed due to the flexibility of the right and left bases 6a and 7a. Thereby, the right and left connectors 6c and 7c is moved opposite in the left-right direction of the mask 1, so that the engagement between the right rod 6c2 and the right groove 4b1 of the right connector 4b and the engagement between the left rod 7c2 and the left groove 4c1 of the left connector 4c are released. The right rod 6c2 comes to be engageable with another right groove 4b1. The left rod 7c2 comes to be engageable with another left groove 4c1.

With the right and left rods 6c2 and 7c2 respectively opposed to other right and left grooves 4b1 and 4c1, when the right and left support parts 6 and 7 are press-released, the wall section 2 elastically returns to its original shape and the right and left connectors 6c and 7c are moved outwards in the left-eight direction of the mask 1, so that the right and left rods 6c2 and 7c2 are engaged with the above-mentioned right and left grooves 4b1 and 4c1. Thereby, the right and left connection parts 4b and 4c respectively rotate about the right and left protrusions 4b2 and 4c2, so that the relative position between the communication section 4 and the wall section 2 changes. Thus, the arrangement of the expired gas introduction section 4 coupled with the communication section 4 with respect to the wall section 2 is changed in the forward-rearward direction in the internal space 2b of the wall section 2.

As set forth from the foregoing, the right and left connectors 6c and 7c of the right and left support parts 6 and 7, and the right and left connection parts 4b and 4c of the communication section 4 constitute an adjusting mechanism 8 which adjusts the position of the communication section 4 supported by the wall section 2.

According to this configuration, the initial position of the expired gas introduction section 3 in the internal space 2b is changeable depending upon the facial shape of subject to which the mask 1 is attached. For example, the expired gas is introduced into the position at which the expired gas introduction section 3 cannot contact the subject's nose or into which the expired gas can be more surely introduced. Accordingly, the expired gas is surely introduced into the expired gas concentration detection sensor regardless of subject's facial shapes.

Particularly, since the position at which the communication section 4 is supported by the wall section 2 with the elastic deformation of the wall section 2 is adjustable in the adjusting mechanism 8, a complicated structure is not required. Accordingly, the expired gas is surely introduced into the expired gas concentration sensor regardless of the difference in the subject's facial shapes, without excessively increasing the cost.

As shown in FIG. 4A, the communication section 4 is further provided with a sensor support 4d. The sensor support 4d has a middle part 4d1, a right part 4d2, and a left part 4d3. The middle part 4d1 is provided in front of the connection part 4a. The right part 4d2 extends rightwards from the middle part 4d1. The left part 4d3 extends leftwards from the front side of the connection part 4a.

Figure 5A:
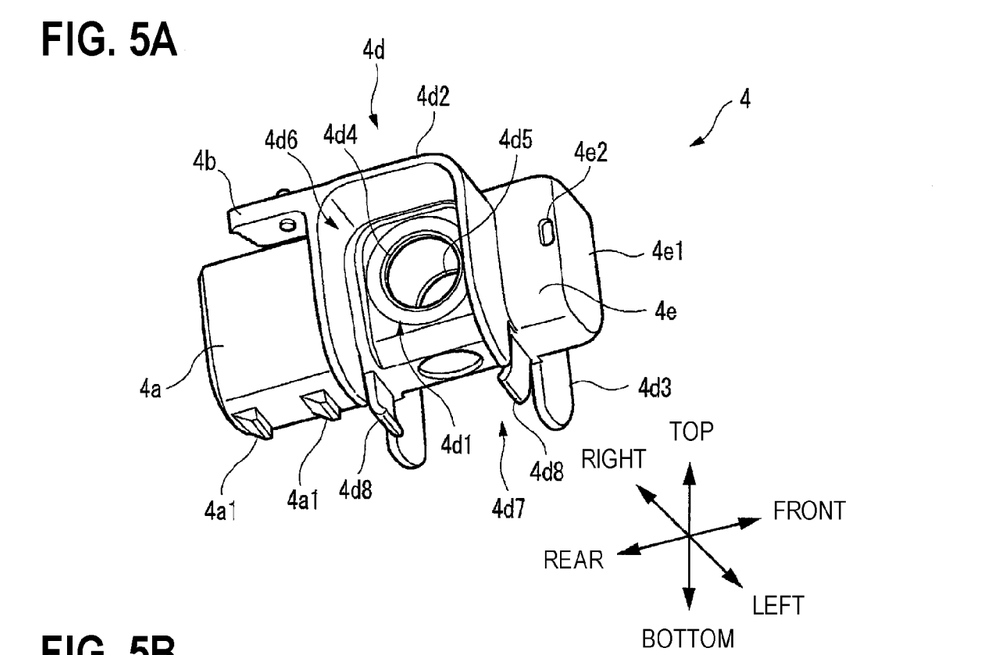
FIGS. 5A and 5B are perspective views of a communication section and a sensor to be provided in the mask.

FIG. 5A is a perspective view showing an appearance of the lower portion of the communication section 4 when viewed from the right front side thereof. The middle part 4d1 defines a detection space which communicates with the communication channel defined by the connection part 4a. Thus, the detection space forms a portion of the communication channel. The right side of the middle part 4d1 is provided with a right light-transparent window 4d4. The left side of the middle part 4d2 is provided with a left light-transparent window 4d5. The right part 4d2 defines a right holding space 4d6 which opens downwards. The right window 4d4 is disposed in the right holding space 4d6. The left part 4d3 defines a left holding space 4d7 which opens downwards. The left window 4d5 is disposed in the left holding space 4d7. The middle part 4d1 is provided on the lower surface thereof with a pair of engaging pieces 4d8.

Figure 5B:
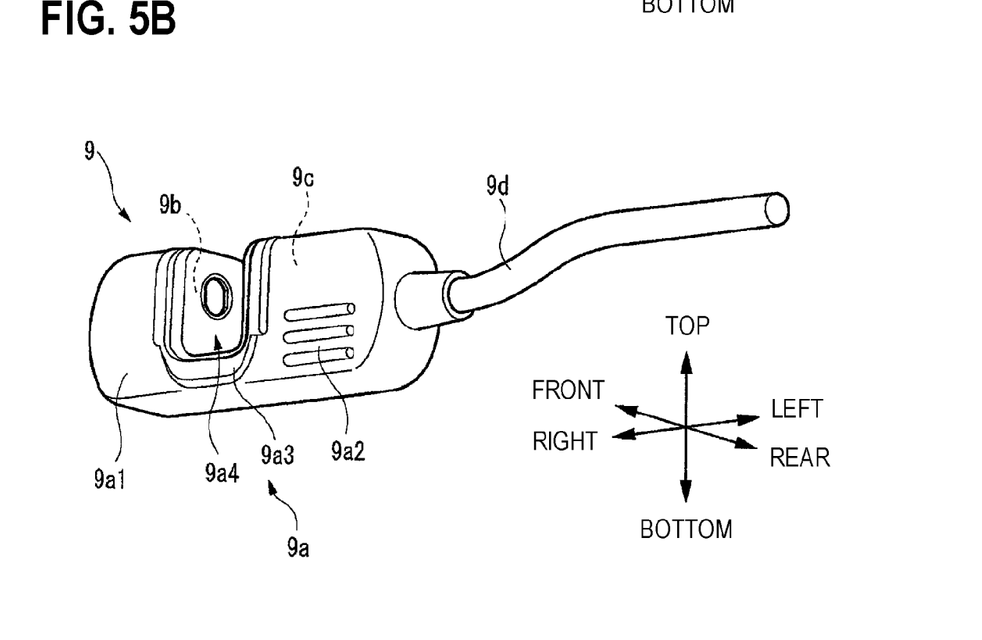

FIG. 5B is a perspective view showing an appearance of a sensor 9 which is mounted to the sensor support 4d. As an expired gas concentration detection sensor, the sensor 9 is provided with a housing 9a. The housing 9a has a first to third parts 9a1, 9a2, and 9a3. The first and second parts 9a1 and 9a2 are connected by the third part 9a3, thereby defining a recessed part 9a4.

The sensor 9 is provided with a light-emitting device 9b and a light-receiving device 9c. The light-emitting device 9b is accommodated in the first part 9a1 of the housing 9a. The light-receiving device 9c is accommodated in the second part 9a2 of the housing 9a. The light-emitting device 9b and the light-receiving device 9c are opposed each other from the recessed part 9a4. A cord 9d is connected to the sensor 9. The cord 9d includes a signal line which transmits a drive signal for a light-emitting device 9b and a light-detection signal by the light-receiving device 9c to a display which is not shown.

Figure 6:
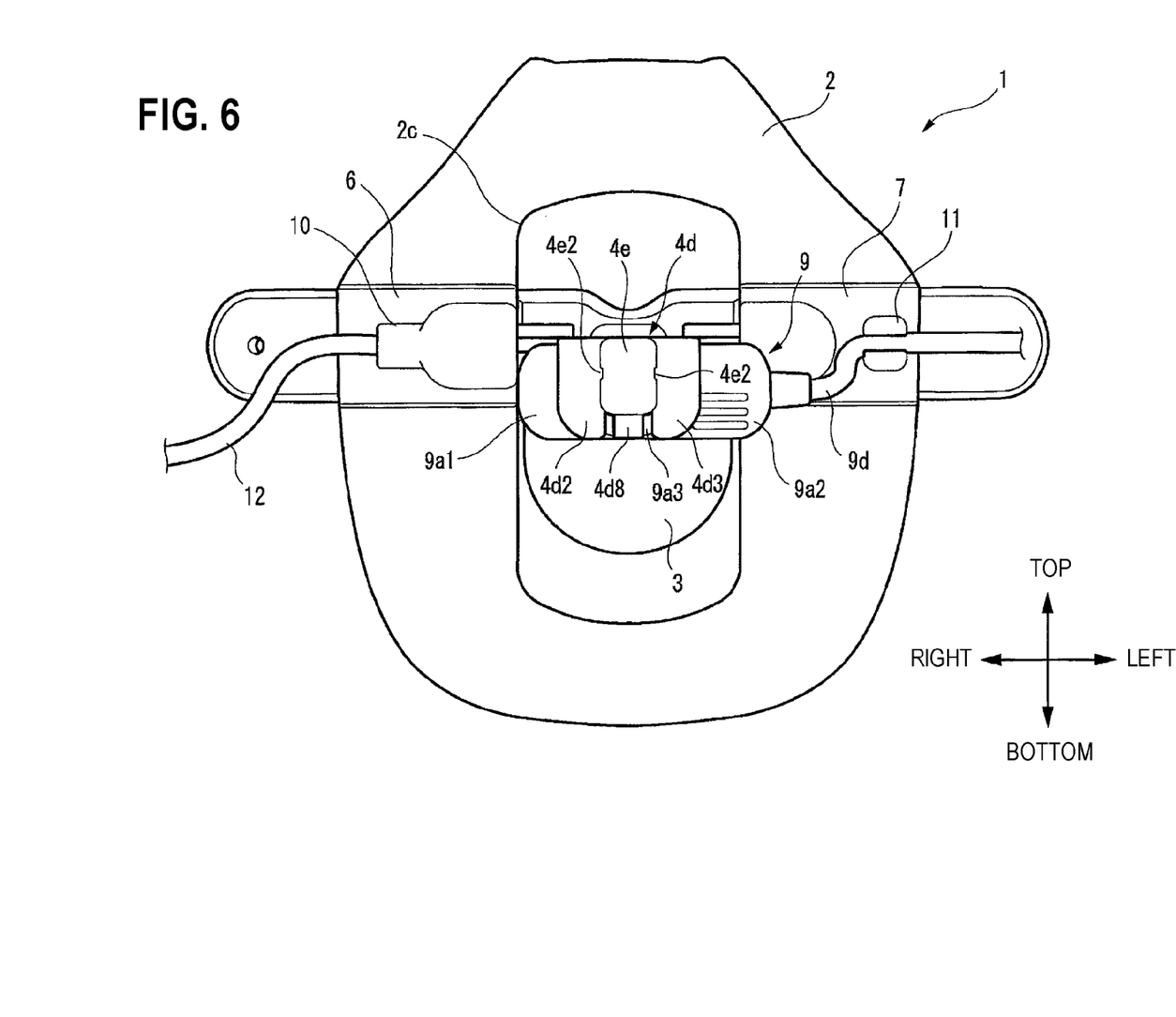
FIG. 6 is a front view of the sensor being mounted on the mask of FIG. 1.

A description will be made of the sensor 9 being mounted to the communication section 4, with reference to FIGS. 5 and 6. FIG. 6 is a front view showing an appearance of the mask 1 in which the sensor 9 is mounted to the sensor support 4d. The sensor 9 is mounted such that the middle part 4d1 of the sensor support 4d is fitted into the recessed part 9a4. An engaging protrusion 4d8 formed on the middle part 4d1 is engaged with the third part 9a3 of the housing 9a. Accordingly, the first part 9a1 of the housing 9a is held in the right holding space 4d6 defined by the right part 4d2. The second part 9a2 of the housing 9a is held in the left holding space 4d7 defined by the left part 4d3. Here, the light-emitting device 9b is opposed to the right window 4d4, and the light-receiving device 9c is opposed to the left window 4d5. That is, the sensor support 4d supports the sensor 9 such that light emitted from the light-emitting device 9b passes across a portion of the communication channel.

Light emitted from the light-emitting device 9b enters the detection space defined in the middle part 4d1 via the right window 4d4. Into the detection space, the expired gas introduced from the expired gas introduction section 3 is introduced via the communication channel defined by the connection part 4a of the communication section 4. Light passing through the detection space reaches the light-receiving device 9c via the left window 4d5. Light emitted from the light-emitting device 9b has a wavelength capable of absorbing carbon dioxide as an example of the expired gas. Since the intensity of light which reaches the light-receiving device 9c varies depending upon the concentration of carbon dioxide contained in the subject's expired gas, the concentration of carbon dioxide contained in the expired gas is detected by monitoring the intensity of light.

As shown in FIG. 5A, the communication section 4 is further provided with a vent part 4e. The vent part 4e is provided in front of the middle part 4d1, and defines an internal space which communicates with the detection space defined by the middle part 4d1. Accordingly, the internal space forms a portion of the communication channel. A front end surface of the vent part 4e forms a closed wall 4e1. That is, the front end of the communication channel, which extends in the direction perpendicular to the movement direction of light emitted from the light-emitting device 9b, is closed.

The vent part 4e is provided with a vent hole 4e2 on the front right side. As shown in FIG. 6, the vent part 4e is also provided with the same vent hole 4e2 on the front left side. The respective vent hole 4e2 allows the outside of the wall section 2 and the communication channel to communicate with each other. The expired gas introduced into the communication section 4 through the expired gas introduction section 3 is discharged out through the respective vent holes 4e2. That is, the respective vent holes 4e2 allow the communication channel and the outside of the wall section 2 to communicate with each other.

Since the vent hole 4e2 is arranged at a position that strays out of the detection space (a portion of the communication channel) across which light emitted from the light-emitting device 4b passes, the introduction of external air into the detection space which is accompanied by the ventilation is prevented. This prevents an inverse affection of the introduction of external air on the detection of the expired gas concentration in the detection space. Further, the expired gas is quickly discharged via the vent holes 4e2. Accordingly, along with the above-mentioned function of regulating the position of the expired gas introduction section 3, there is provided a function of precisely detecting the concentration of the subject's expired gas.

As shown in FIG. 1, the mask 1 is further provided with an oxygen-supply section 10 and a cord-holding section 11. The oxygen-supply section 10 is disposed at a front side of the right support parts. The cord-holding section 11 is disposed at a frond side of the left support parts.

The oxygen-supply section 10 holds an end of an oxygen-supply tube 12. The oxygen-supply tube 12 may be integrally formed with the oxygen-supply section 12, or otherwise may be detachably attached to the oxygen-supply section 10. Although not shown in the drawings, the inside of the oxygen-supply section 10 communicates with the internal space 2b of the wall section 2. Oxygen supplied from the outside through the oxygen-supply tube 12 is provided through the internal space 2b in response to the subject's inspiration.

Here, the right and left bridge parts 5a and 5b scatter oxygen to be injected into the internal space 2b from the oxygen-supply section 10. Thereby, the concentration of oxygen in the internal space 2b is homogenized. Further, oxygen to be injected into the internal space 2b from the oxygen-supply section 10 does not directly contact the subject's face, thereby preventing the skin from becoming dry.

The cord-holding section 11 detachably holds a cord 9d which is connected to the sensor 9. FIG. 6 shows the cord 6d being held by the cord-holding section 11. Further, the oxygen-supply section 10 and the cord-holding section 11 are arranged symmetrically in the left-right direction of the mask 1, with the sensor support 4d of the communication section 4 interposed therebetween.

According to this configuration, the oxygen-supply tube 12 and the cord 9d is drawn symmetrically in the left-right direction of the mask 1, so it is possible to stabilize the posture of the mask 1 with respect to the subject's face. Accordingly, along with the above-mentioned function of regulating the position of the expired gas introduction section 3, there is provided both the function of precisely detecting the concentration of the subject's expired gas and the function of stably supplying oxygen to the subject.

The above-mentioned embodiments are merely provided for illustrative purposes, but not limitative purposes. It is apparent that the presently disclosed subject matter may be changed/modified without departing from the spirit of the presently disclosed subject matter, and that the equivalents of the presently disclosed subject matter are included in the scope of the presently disclosed subject matter.

When the mask 1 includes at least one of the flexibility of the right and left bridge parts 5a and 5b, the slidability of the connection part 3e of the expired gas introduction section 3 with respect to the connection part 4a of the communication section 4, and the adjusting mechanism 8, the position of the expired gas introduction section 3 in the internal space 2b of the wall section 2 is variable.

In the case where the adjusting mechanism 9 is omitted, the communication section 4 may not essentially be supported by the wall section 2. For example, the communication section may be supported by the expired gas introduction section 3, for example.

The configuration of the sensor support 4d of the communication section 4 may be properly changed depending upon the specification of the sensor 9. For example, the sensor 9 in the former embodiment includes the housing 9a in which an accommodation part for the light-emitting device 9b and an accommodation part for the light-receiving device 9c are integrally formed. However, the accommodation part for the light-emitting device 9b and the accommodation part for the light-receiving device 9c may be separately formed.

What is claimed is:

1. A mask configured to be attached to a face of a subject, the mask comprising:
   a wall section that defines an internal space and is adapted to cover at least a portion of a nose and a mouth of the subject;
   an expired gas introduction section that is disposed in the internal space and is adapted to introduce expired gas of the subject; and
   a communication section that defines a communication channel through which the expired gas is delivered from the expired gas introduction section into an expired gas concentration detection sensor, the expired gas concentration detection sensor being detachably mounted to the communication section,
   wherein a position of the expired gas introduction section in the internal space is variable, and
   wherein the communication section and the expired gas introduction section are coupled so as to be relatively movable with respect to each other in a rear-front direction of the mask, and
   wherein the communication section and the expired gas introduction section are relatively movable with respect to each other in a linear direction.

2. The mask according to claim 1, wherein the communication section and the expired gas introduction section are slidably coupled so as to be slidable with respect to each other.

3. The mask according to claim 1, wherein:
   the one of the communication section and the expired gas introduction section includes a plurality of protrusions and the other of the communication section and the expired gas introduction section includes an engaging part, and
   the communication section and the expired gas introduction section are movably coupled such that a position of the expired gas introduction part with respect to the communication section is adjustable by selecting one of the protrusions to be engaged with the engaging part.

4. A mask adapted to be attached to a face of a subject, the mask comprising:
   a wall section that defines an internal space and is adapted to cover at least a portion of a nose and a mouth of the subject;
   an expired gas introduction section that is disposed in the internal space and is adapted to introduce expired gas of the subject;
   a communication section that defines a communication channel through which the expired gas is delivered from the expired gas introduction section to an expired gas concentration detection sensor; and
   an adjusting mechanism that is configured to adjust a supporting position at which the communication section is supported by the wall section, the adjusting mechanism including a first connecting part defined by the communication section and a second connecting part defined by a support part attached to the wall section, the second connecting part being engaged with the first connecting part.

5. The mask according to claim 4, wherein
   a position of the expired gas introduction section in the internal space is variable, and
   the expired gas introduction section is supported by the communication section.

6. The mask according to claim 5, wherein
   the adjusting mechanism includes a mechanism that adjusts the supporting position by elastic deformation of the wall section.

7. The mask according to claim 4, wherein the adjusting mechanism includes a plurality of grooves and a rod engaged with one of grooves.

8. The mask according to claim 7, wherein the first connecting part corresponds to one or the rod and the plurality of grooves, and the second connecting part corresponds to the other of the rod and the plurality of grooves.

9. The mask according to claim 4, wherein the support part is made of a harder material than the wall section.

10. A mask configured to be attached to a face of a subject, the mask comprising:
- a wall section that defines an internal space and is adapted to cover at least a portion of a nose and a mouth of the subject;
- an expired gas introduction section that is disposed in the internal space and is adapted to introduce expired gas of the subject; and
- a communication section that defines a communication channel through which the expired gas is delivered from the expired gas introduction section into an expired gas concentration detection sensor,
- wherein the expired gas introduction section includes a partition part which defines a first opening part adapted to open against the face of the subject when the mask is attached to the face of the subject, and which defines a second opening part opening upwards and being a single opening adapted to cover nostrils of the subject only from a lower side when the mask is attached to the face of the subject,
- wherein the first opening part and the second opening part are disposed in the internal space, and
- wherein the partition part includes a wall member, a long side of the wall member extending in a horizontal direction and a short side of the wall member extending in a vertical direction.

11. The mask according to claim 10, wherein a position of the expired gas introduction section in the internal space is variable.

12. The mask according to claim 10, wherein the partition part has: an upper body that includes the wall member and defines the first opening part; and a lower body that defines the second opening part, and the wall member is adapted to face a part of the face of the subject under the nostrils of the subject when the mask is attached to the face of the subject.

13. A mask adapted to be attached to a face of a subject, the mask comprising:
- a wall section that defines an internal space and is adapted to cover at least a portion of a nose and a mouth of the subject;
- an expired gas introduction section that is disposed in the internal space and is adapted to introduce expired gas of the subject;
- a communication section that defines a communication channel through which the expired gas is delivered from the expired gas introduction section to an expired gas concentration detection sensor;
- an oxygen-supply section that communicates with the internal space, and that is configured to hold one end of an oxygen-supply tube; and
- a holding section defining an opening portion that opens in a direction away from the wall section, wherein the communication section is arranged laterally between the oxygen-supply section and the holding section, along a left-right direction of the mask.

14. The mask according to claim 13, wherein the holding section is fixed to a front side of a support part attached to the wall section, wherein the support part is made of a harder material than the wall section.

15. The mask according to claim 14, the holding portion extends from the support part in a rear-front direction of the mask, and the opening portion opens in the rear-front direction.

16. A mask adapted to be attached to a face of a subject, the mask comprising:
- a wall section that defines an internal space and is adapted to cover at least a portion of a nose and a mouth of the subject;
- an expired gas introduction section that is disposed in the internal space and is adapted to introduce expired gas of the subject; and
- a communication section that defines a communication channel through which the expired gas introduced from the expired gas introduction section is introduced to an expired gas concentration detection sensor,
- wherein the communication section has an elongated shape,
- the communication section includes a vent hole at an end portion in a longitudinal direction thereof, the vent hole through which an outside of the wall section and the communication channel communicate with each other, and
- when the mask is attached to the face of the subject, the communication channel is disposed between the face of the subject and the vent hole.

17. The unit according to claim 16, wherein:
the communication channel includes a detection space that is detected by the expired gas concentration detection sensor, and
the vent hole is arranged along the communication channel downstream of the detection space.

18. A mask unit adapted to be attached to a face of a subject, the mask unit comprising:
a mask including:
- a wall section that defines an internal space and is adapted to cover at least a portion of a nose and a mouth of the subject;
- an expired gas introduction section that is disposed in the internal space and is adapted to introduce expired gas of the subject; and
- a communication section that defines a communication channel through which the expired gas is delivered from the expired gas introduction section to the expired gas concentration detection sensor; and
- a single oxygen-supply tube that is attached to one side face of the mask and communicates with the internal space, wherein the oxygen-supply tube is held on the mask such that the oxygen-supply tube extends only in one of left and right directions from the one side face of the mask,
- wherein the expired gas concentration detection sensor has a single cord, the cord extending in the other of the left and right directions from the mask, and
- wherein the oxygen-supply tube and the cord symmetrically extend along the mask.

19. The mask unit according to claim 18, wherein the mask includes a bridge part that is extended from the wall section to an outside.

* * * * *